(12) United States Patent  
Janik et al.

(10) Patent No.: US 7,369,235 B1
(45) Date of Patent: May 6, 2008

(54) METHOD AND SYSTEM FOR MEASURING DEEP TRENCHES IN SILICON

(75) Inventors: Gary R. Janik, Palo Alto, CA (US); John Fielden, Los Altos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 164 days.

(21) Appl. No.: 11/165,711

(22) Filed: Jun. 24, 2005

(51) Int. Cl.
*G01J 4/00* (2006.01)

(52) U.S. Cl. ...................................... 356/369

(58) Field of Classification Search ............ None
See application file for complete search history.

(56) References Cited

U.S. PATENT DOCUMENTS

| | | |
|---|---|---|
| 5,329,357 A | 7/1994 | Bernoux et al. |
| 5,384,639 A | 1/1995 | Wickramasinghe |
| 5,392,118 A | 2/1995 | Wickramasinghe |
| 5,608,526 A | 3/1997 | Piwonka-Corle et al. |
| 5,739,909 A | 4/1998 | Blayo et al. |
| 5,991,037 A | 11/1999 | Piel et al. |
| 6,483,580 B1 | 11/2002 | Xu et al. |
| 6,590,656 B2 | 7/2003 | Xu et al. |
| 6,704,661 B1 | 3/2004 | Opsal et al. |
| 2004/0119020 A1* | 6/2004 | Bodkin ................. 250/353 |
| 2004/0239933 A1* | 12/2004 | Opsal et al. ........... 356/369 |

* cited by examiner

*Primary Examiner*—Tu T Nguyen
(74) *Attorney, Agent, or Firm*—Bever, Hoffman & Harms, LLP; Jeanette S. Harms

(57) ABSTRACT

A spectroscopic ellipsometry system directs a near infra-red (NIR) probe beam at a test sample to allow metrology to be performed on vertical structures within the test sample. Because silicon is relatively transparent to NIR light, structural information can be determined from the polarization effects produced by the test sample, in a manner similar to that used with IR spectroscopic ellipsometry systems. However, unlike IR light, which requires delicate and costly optical and measurement components (e.g., vibration-sensitive Fourier transform sensors), NIR light can be directed and detected using more robust and inexpensive components (e.g., array-based detectors), thereby making a NIR spectroscopic ellipsometry system much more affordable and usable than conventional IR spectroscopic ellipsometry systems.

12 Claims, 4 Drawing Sheets

METHOD AND SYSTEM FOR MEASURING DEEP TRENCHES IN SILICON

BACKGROUND OF THE INVENTION

1. Field of the Invention

The invention relates to the field of semiconductor metrology, and in particular to a system and method for characterizing small trenches formed in silicon.

2. Related Art

Traditionally, semiconductor devices such as metal-oxide-semiconductor (MOS) transistors have been formed as essentially planar devices (sometimes referred to as "bulk" devices). Specifically, the gate dielectric and gate elements in such devices have been flat structures formed on the surface of a silicon wafer. However, in modern semiconductor devices, the need to achieve higher device performance in reduced die areas has led to the development of device designs that make greater use of the vertical dimension. For example, a "tri-gate" transistor can be formed by etching parallel trenches into a silicon wafer, thereby creating a "fin" of silicon between the trenches. A gate dielectric layer and a gate layer can then be formed that wrap over the surface of the fin, thereby creating a gate and channel structure for the transistor. Because the gate can apply an electric field to three surfaces of the channel region, control over current flow through the fin can be enhanced over similarly-sized bulk transistors.

Unfortunately, this trend towards vertical structures within increasingly miniaturized devices can significantly complicate measurements performed on those devices. For example, forming an array of tri-gate transistors requires that a series of trenches be formed in the silicon substrate. To provide the greatest device performance in the smallest die area, the trenches are relatively deep and narrow, which makes interior inspection of individual trenches extremely difficult, particularly because the trench dimensions are typically smaller than the wavelengths of light used in conventional optical metrology tools.

One approach to overcome this measurement difficulty is to use an infra-red (IR) spectroscopic ellipsometry technique to measure an array of trenches as a whole. For example, FIG. 1 shows an IR spectroscopic ellipsometry system 100 that includes a stage 110 for supporting a test sample 190, an IR beam generator 120, focusing optics 130, output optics 140, and a Fourier transform spectrometer (FTS) 150. Test sample 190 includes an array of trenches 191, with each trench having a width W and a depth D. The remaining material between each trench 191 has a width T. Typical trench dimensions for current dynamic random access memory (DRAM) designs could be depths D between 2 μm and 15 μm, and widths W of less than 0.5 μm.

To perform a metrology operation on test sample 190, IR beam generator 120 generates an IR probe beam 121 that focusing optics 130 directs onto test sample 190. IR probe beam 121 includes light from the short to long IR regions having wavelengths across the range of 2 to 20 μm. IR probe beam 121 is reflected by test sample 190 as an output beam 122 that is directed by output optics 140 onto FTS 150. A polarizer 131 in focusing optics 130 and an analyzer 141 in output optics 140 allow polarization changes caused by test sample 190 to be measured by FTS 150.

To analyze the data gathered by FTS 150, the array of trenches 191 is modeled as a "fictitious" film of a material having characteristics falling somewhere between those of air and those of pure silicon. This fictitious film modeling can be performed due to the fact that silicon is essentially transparent to IR light, so that any reflection that occurs (i.e., output beam 122) is a function of the geometry of trenches 191. Furthermore, because the wavelengths of IR probe beam 121 will generally be much larger than the width of trenches 191, output beam 122 will include contributions from many trenches 191. Therefore, the resulting measurements will be representative of the array of trenches as a whole.

Once the characteristics of the fictitious film are determined, those characteristics can be used to generate measurement values for trenches 191. For example, the thickness of the fictitious film can be provided as the measured value for the depth D of trenches 191. Likewise, the index of refraction for the fictitious film can be used to determine a volumetric ratio for the trench (air) and silicon regions, thereby allowing an average width W for trenches 191 to be determined. In this manner, IR spectroscopic ellipsometry system 100 can enable characterization of the array of trenches 191 on test sample 190.

Unfortunately, IR spectroscopic ellipsometry system 100 is faced with several issues that limit its applicability and effectiveness as a metrology tool. First, due to the low reflectivity of silicon to IR light, it is desirable for IR probe beam 121 to have a high intensity to maximize the signal provided by output beam 122. However, the relatively long wavelengths of light in IR probe beam 121 (i.e., low to high IR wavelengths) can make generation of a high intensity difficult. Furthermore, those long wavelengths can also prevent measurements from being taken in small regions of a test sample (e.g., in the scribe line of a wafer), thereby limiting the flexibility of IR spectroscopic ellipsometry system 100.

Finally, the main issue affecting the feasibility of IR spectroscopic ellipsometry system 100 as a production tool is the high cost and complexity of the components required for IR signal processing. For example, due to chromatic aberration effects that increase with increased wavelength, high-precision mirrors must generally be used in focusing optics 130 and output optics 140, rather than more inexpensive lenses. In addition, because typical CCD (charge coupled device) and diode arrays are unable to sense wavelengths above roughly 900 nm, IR spectroscopic ellipsometry system 100 requires the use of FTS (Fourier transform sensor) 150. FTS 150 incorporates beam splitting optics 151 and an interferometer 152 that allows a Fourier transform to be performed on output beam 122 to generate a spectrum of intensities for the range of wavelengths in output beam 122. FTS 150 is a very complex and expensive sensor that is also very delicate and extremely sensitive to vibrations, and is therefore not particularly well-suited for a production environment.

Accordingly, it is desirable to provide a robust, reliable, and low-cost system and method for performing metrology on trenches in a silicon substrate.

SUMMARY OF THE INVENTION

Conventional IR spectroscopic ellipsometry systems provide a means for measuring the characteristics of trenches in silicon that would be difficult to otherwise determine. However, the IR handling components required by such systems are expensive and delicate, and can therefore reduce the practical utility of an IR spectroscopic ellipsometry system. By performing spectroscopic ellipsometry using a probe beam in the near IR (NIR) range, the metrology capabilities of IR spectroscopic ellipsometry can be provided without the need for the costly and fragile IR-compatible components required by conventional IR spectroscopic ellipsometry systems.

For example, in one embodiment, a NIR spectroscopic ellipsometry system can include a NIR probe beam generator, focusing optics (including a polarizer), output optics (including an analyzer), a detector, and an analysis system. To perform a metrology operation, NIR probe beam generator produces a NIR probe beam that includes light in the near IR range (i.e., wavelengths in the range of approximately 0.7 to 2.0 μm). The focusing optics direct the NIR probe beam onto the test sample, and the reflected output beam is directed by output optics onto the detector. The use of NIR light allows the detector to be an array-based detector, which is much less expensive and much less sensitive to environmental factors (e.g., vibration) than the FTS sensor used in conventional IR spectroscopic ellipsometry systems. In one embodiment, the NIR spectroscopic ellipsometry system can include multiple detectors that measure different ranges of the NIR light in the reflected beam.

The data gathered by the detector(s) can then be analyzed by the analysis system to generate measurement data for the test sample. In one embodiment, the analysis algorithms can be substantially similar to those used in IR spectroscopic ellipsometry systems. For example, the analysis system in a NIR spectroscopic ellipsometry system can include fictitious layer modeling logic for modeling structures on the test sample (e.g., an array of trenches) as a fictitious layer of homogenous material. By varying the properties of this fictitious layer (e.g., thickness and index of refraction) until the optical behavior of the fictitious layer matches the actual measurement data, measurement properties (e.g., trench dimensions, porosity, void content, thickness of porous layer) for the structures in the test sample can be determined.

The invention will be more fully understood in view of the following description and drawings.

DETAILED DESCRIPTION

Conventional IR spectroscopic ellipsometry systems provide a means for measuring the characteristics of trenches in silicon that would be difficult to otherwise determine. However, the IR handling components required by such systems are expensive and delicate, and can therefore reduce the practical utility of an IR spectroscopic ellipsometry system. By performing spectroscopic ellipsometry using a probe beam in the near IR (NIR) range, the metrology capabilities of IR spectroscopic ellipsometry can be provided without the need for the costly and fragile IR-compatible components required by conventional IR spectroscopic ellipsometry systems.

Figure 2A:
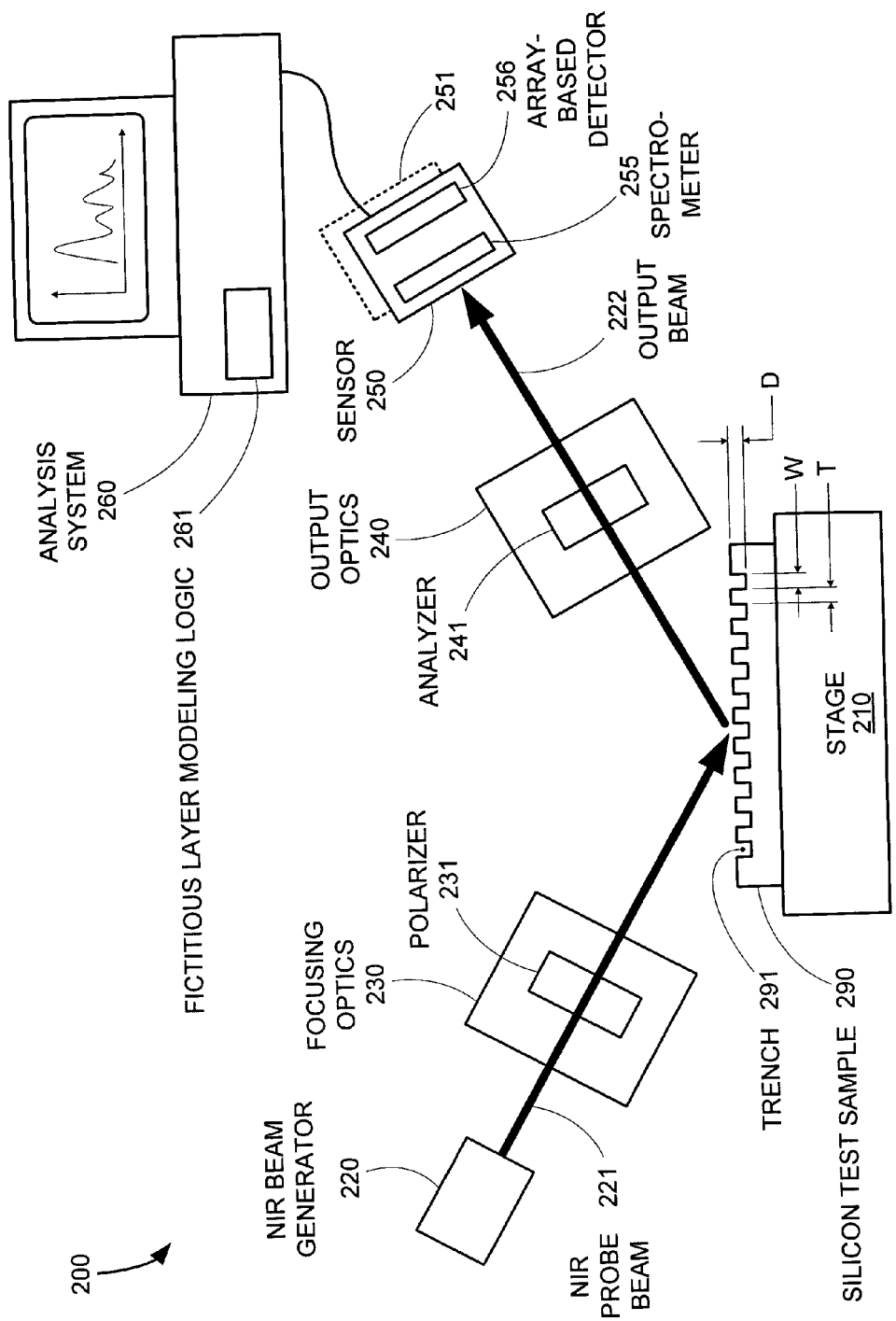
FIG. 2A is a block diagram of a NIR spectroscopic ellipsometry system.

FIG. 2A shows a NIR spectroscopic ellipsometry system 200 for analyzing a silicon test sample 290. NIR spectroscopic ellipsometry system 200 includes a stage 210, a NIR beam generator 220, focusing optics 230, output optics 240, a sensor 250, and an analysis system 260. Test sample 290, which is supported by stage 210, includes an array of trenches 291, with each trench having a width W and a depth D. The remaining material between each trench 291 has a width T. As noted above, typical trench dimensions for current dynamic random access memory (DRAM) designs could be depths D between 2 μm and 15 μm, and widths W of less than 0.5 μm.

To perform a metrology operation on test sample 290, NIR beam generator 220 generates a NIR probe beam 221 that focusing optics 290 directs onto test sample 290. NIR probe beam 221 includes light in the near IR regions having wavelengths somewhere in the range of 0.7 to 2.0 μm. As described in greater detail below, depending on the analysis requirements and the capabilities of sensor 250, the actual wavelengths in NIR probe beam 221 can span any range, such as from 0.7 to 0.9 μm, from 0.7 to 1.0 μm, from 1.0 to 2.0 μm, or from 0.7 to 2.0 μm, among many others. NIR probe beam 221 is reflected by test sample 290 as an output beam 222, which is directed by output optics 240 onto sensor 250. Note that in various embodiments, NIR spectroscopic ellipsometry system 200 can include any number of sensors, as indicated by optional sensor 251 (shown using a dotted outline).

Polarization elements such as polarizer 231 and analyzer 241 in focusing optics 230 and analyzing optics 240, respectively, allow sensor 250 to measure the change in polarization caused by the interaction of test sample 290 with NIR probe beam 221. Sensor 250 can include a spectrometer 255 and an array detector 256. Spectrometer 255 can comprise a reflection grating, a transmission grating, a prism, or any other type of dispersive element to disperse the various wavelength components making up output beam 222. This dispersion allows array detector 256 to measure different wavelength components on different pixels to enable the collection of a spectroscopic signal for output beam 222.

Note that while a single polarizer 231 and a single analyzer 241 are depicted in FIG. 2A for exemplary purposes, in various other embodiments, focusing optics 230 and output optics 240 can include any number and type of optical elements (e.g., filters, collimators, compensators, and quarter wave plates) to allow any type of spectroscopic ellipsometry to be performed. For example, in one embodiment, polarizer 231 could be a rotating polarizer, while in another embodiment, analyzer 241 could be a rotating analyzer. In another embodiment, focusing optics 230 could include a compensator (either static or rotating) to convert the linearly polarized NIR probe beam 221 into a circularly polarized beam. In another embodiment, system 200 can include optional angular adjustment mechanisms (not shown for clarity) for any or all of stage 210, NIR beam generator 220, focusing optics 230, output optics 240, and sensor 250 to allow variable angle spectroscopic ellipsometry (VASE) to be performed using NIR probe beam 221.

Figure 1:
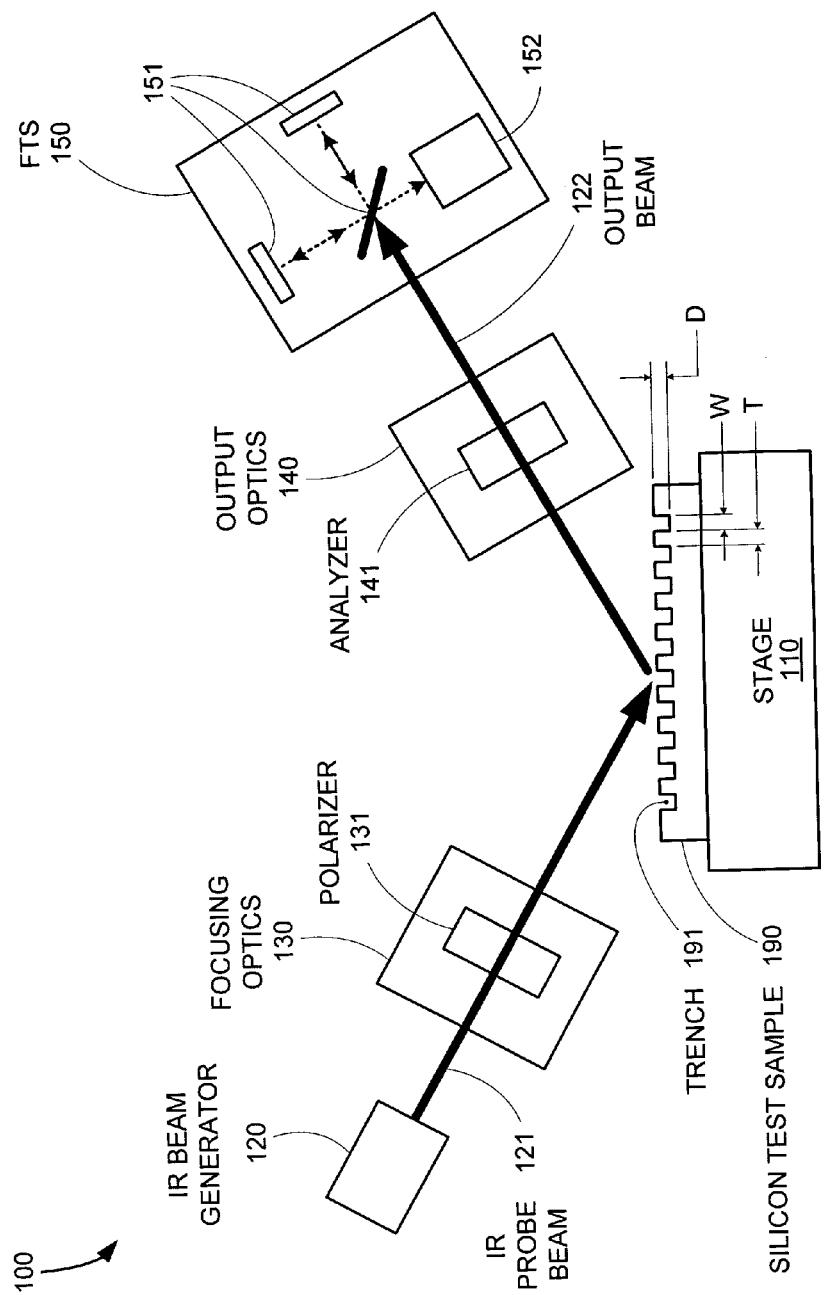
FIG. 1 is a block diagram of a conventional IR spectroscopic ellipsometry system.

The measurements taken by sensor 250 are then analyzed by analysis system 260 to generate measurement data for test sample 290. Because silicon is still relatively transparent to the near IR wavelengths, the data can be evaluated in a manner substantially similar to analysis methods used in conventional IR spectroscopic ellipsometry systems (such as system 100 shown in FIG. 1). For example, the "fictitious layer" technique described above with respect to FIG. 1 can be used by analysis system 260 to determine the characteristics of test sample 290. Specifically, because of the relative transparency of test sample 290 to NIR probe beam 221, the properties of output beam 222 will be highly dependent on the structure of trenches 291 in test sample 290. Therefore, analysis system 260 can include fictitious layer modeling logic 261 to process the measurement data collected from sensor 250. Note that in various embodiments, analysis system 260 can be any type analysis system, such as a personal computer, a thin client running software accessed from a remote server, or embedded logic within sensor 250, among others. Likewise, fictitious layer modeling logic 261 can be any type of logic for performing fictitious layer-based analysis (as described in greater detail below), such as a software program or hard-coded logic (e.g., a programmable logic controller, or PLC).

Figure 2B:
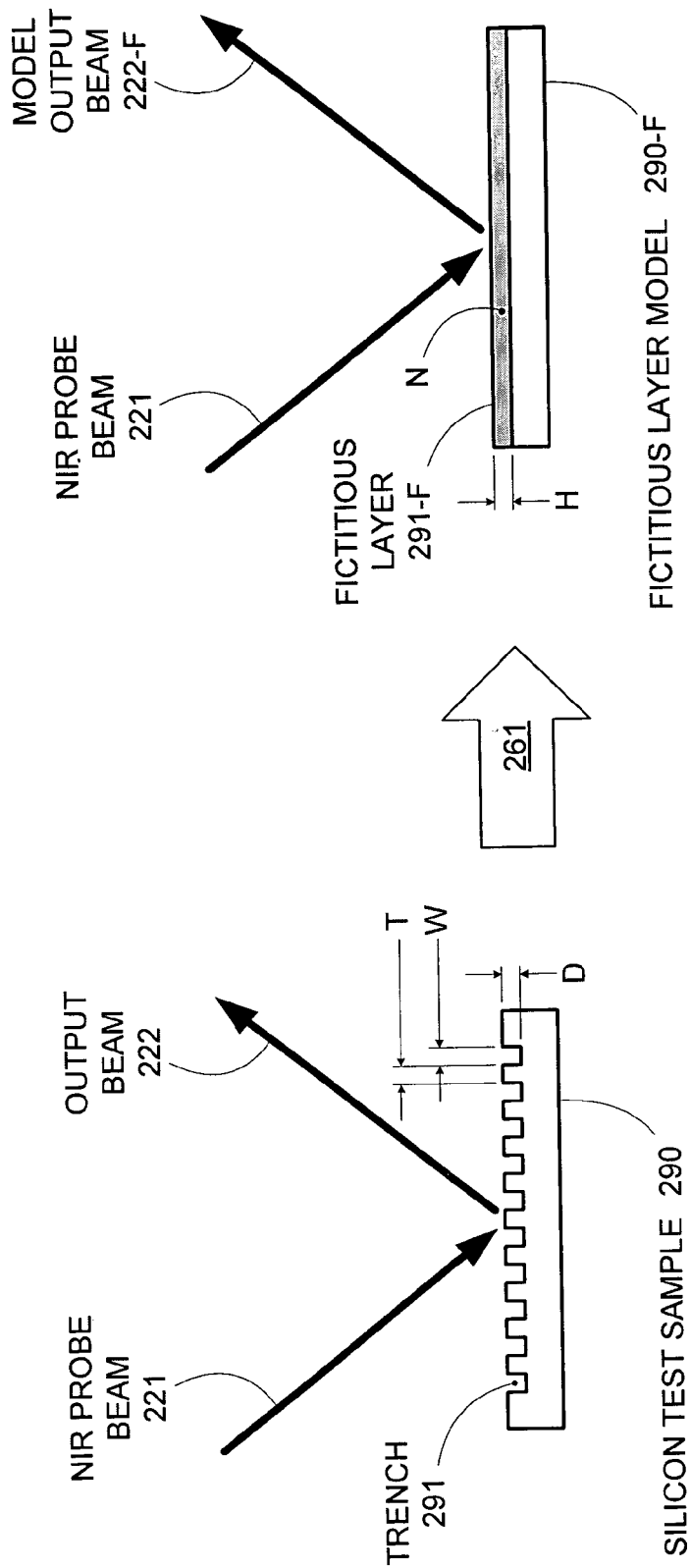
FIG. 2B is a block diagram of an analytical technique for the NIR spectroscopic ellipsometry system of FIG. 2A.

An exemplary fictitious layer modeling operation is depicted in FIG. 2B. In FIG. 2B, silicon test sample 290, which includes an array of trenches 291, is modeled by fictitious layer modeling logic 261 as a test sample 290-F that includes a fictitious layer 291-F. Fictitious layer 291-F is a homogenous layer having a thickness H and an index of refraction N. Thickness H and index of refraction N can then be adjusted until the behavior of fictitious layer model 290-F (i.e., the characteristics of a model output beam 222-F generated in response to NIR probe beam 221) matches the actual measured data for test sample 290 (i.e., the characteristics of output beam 222).

Once a match is detected, thickness H of fictitious layer 291-F can be provided as the depth D of trenches 291. Index of refraction N can be used to determine similar width information for trenches 291. Specifically, index of refraction N is based on the ratio of air (trench) to silicon in the array of trenches 291 in test sample 290. Thus, for example, index of refraction N for fictitious layer 291-F will increase as trenches 291 are reduced in width (i.e., as W decreases and T increases the ratio of silicon (n=3.6) to air (n=1) for the trench array increases, thereby causing the index of refraction N for fictitious layer 291-F to more closely approach that of silicon). Therefore, based on the model index of refraction N, measured values for width W and spacing T can be determined. In this manner, the data provided by output beam 222 as reflected from silicon test sample 290 can be evaluated using fictitious layer model 290-F to determine the characteristics of trenches 291. Note that using a similar methodology, voids, porosity, and the thickness of porous silicon films can also be determined.

Note that while NIR spectroscopic ellipsometry system 200 shown in FIG. 2A can provide the same types of metrology capabilities as conventional IR spectroscopic ellipsometry systems (e.g., system 100 in FIG. 1), NIR spectroscopic ellipsometry system 200 can be constructed using less expensive and more robust components than those conventional IR spectroscopic ellipsometry systems. For example, whereas typical IR generators (e.g., IR beam generator 120 in FIG. 1) typically cannot produce high-intensity IR beams (e.g., IR probe beam 121 in FIG. 1), a near IR beam (e.g., NIR probe beam 221) can be efficiently produced by normal visible light sources such as high-pressure xenon lamps or tungsten filament lamps (with optional collimating and/or filtering optics). Consequently, a stronger output signal (i.e., output beam 222) can be produced using NIR probe beam 221 than would be possible with an IR probe beam, thereby resulting in a generally higher signal to noise ratio for measurements taken by NIR spectroscopic ellipsometry system 200. In addition, the shorter wavelengths of light in NIR probe beam 221 allow NIR probe beam 221 to be focused down to a smaller spot size than would be possible with an IR probe beam, thereby allowing NIR spectroscopic ellipsometry system 200 to take measurements in locations that would be too small for IR spectroscopic ellipsometry systems (e.g., in the scribe line of a production wafer).

Furthermore, because glass lenses are generally ineffective for IR light, an IR spectroscopic ellipsometry system will typically require optical systems (e.g., focusing optics 130 and output optics 140 in FIG. 1) that are based on high-precision mirrors. In contrast, the use of light in the NIR range allows NIR spectroscopic ellipsometry system 200 to replace many of those expensive mirrors with more cost-effective lenses. Also, because array-based detectors such as CCD arrays or photodiode arrays can be used to detect NIR light, NIR spectroscopic ellipsometry system 200 does not require the Fourier transform sensor (FTS 150 in FIG. 1) used in conventional IR spectroscopic ellipsometry systems.

Implementing sensor 250 using an array-based detector 256 can significantly improve the reliability and robustness of NIR spectroscopic ellipsometry system 200 over conventional IR spectroscopic ellipsometry system 100. In some embodiments, different sensors 250 can be used to measure different ranges of NIR light in output beam 222. For example, sensor 250 could be a CCD or a silicon photodiode array to measure NIR light having wavelengths in the range of 0.7 to 0.9 µm, while sensor 251 could be an InGaAs or other compound semiconductor photodiode array to measure NIR light having wavelengths in the range of 1.0 to 2.0 µm. In various other embodiments, NIR spectroscopic ellipsometry system 200 could include only a single sensor 250 for measuring only a portion of (or the entire) the NIR wavelength range.

Note that due to the mechanical similarity of NIR spectroscopic ellipsometry system 200 to conventional UV (ultraviolet) and visible light spectroscopic ellipsometry system, it may be possible to convert a conventional UV/visible spectroscopic ellipsometry system into a NIR spectroscopic ellipsometry system. For example, one such conversion could involve replacing protected aluminum mirror coatings and quartz polarizing elements in a UV/visible spectroscopic ellipsometry system to gold mirror coatings and calcite polarizing elements, respectively, in a NIR spectroscopic ellipsometry system. Of course, the UV/visible light detectors would typically need to be replaced with NIR-sensitive detectors, and additional fictitious layer modeling logic (261) would be required for the NIR spectroscopic ellipsometry system, but some cost benefit could be achieved by re-using much of the mechanical aspects of existing UV/visible spectroscopic ellipsometry systems.

Figure 3:
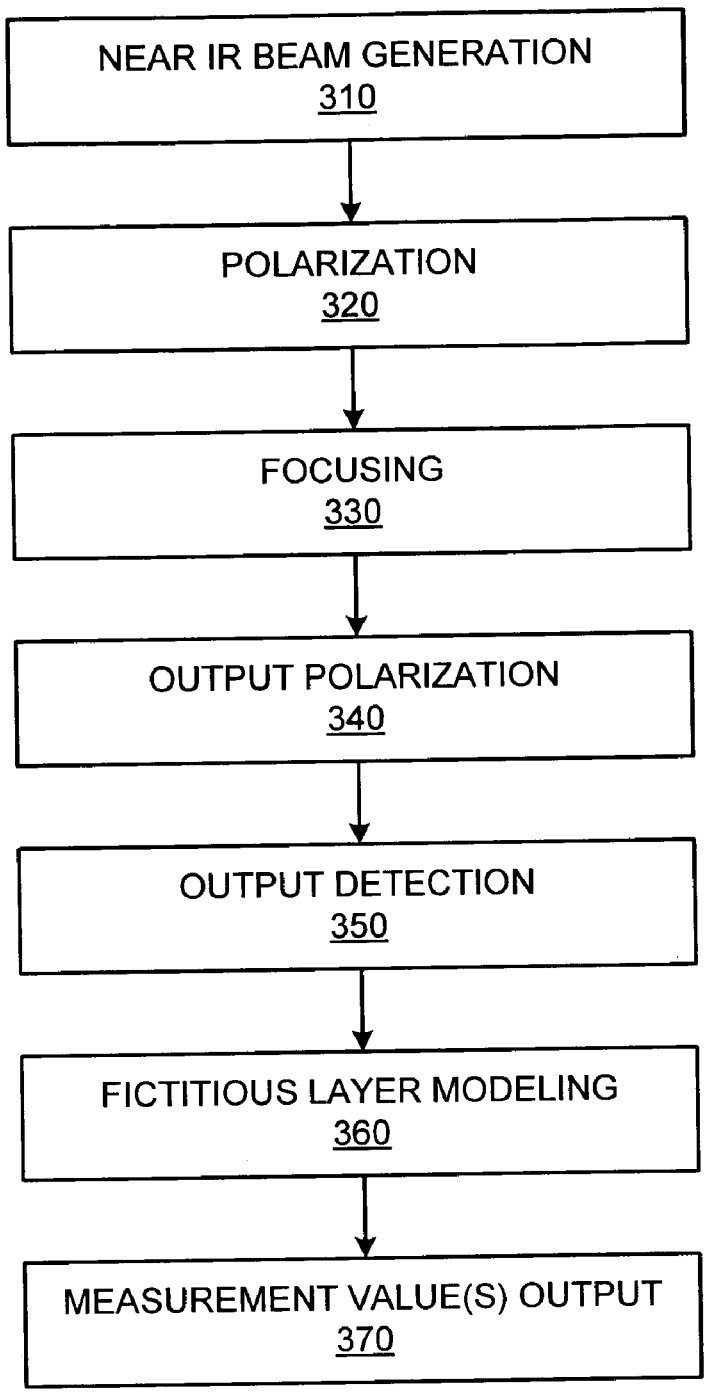
FIG. 3 is a flow diagram of a method for performing metrology on an array of trenches in a silicon substrate.

FIG. 3 shows a flow diagram of a metrology operation using a NIR probe beam, such as described with respect to FIG. 2A. In a "NEAR IR BEAM GENERATION" step 310, a probe beam containing light over a range of near IR wavelengths (NIR probe beam 221) is generated. Then, in a "POLARIZATION" step 320, linear polarization is applied to the NIR probe beam (by polarizer 231). The polarized NIR beam is then directed at the test sample (290) in a "FOCUSING" step 330, and the polarization state of the reflected beam (output beam 222) is detected by an analyzer (241) in an "OUTPUT POLARIZATION" step 340. The signal generated in step 340 is then measured by a detector (250) in an "OUTPUT DETECTION" step 350, and this signal data is processed in a "FICTITIOUS LAYER MODELING" step 360, as described with respect to FIG. 2B. Finally, the results of step 360 are provided as measurement values (e.g., trench dimensions, void presence, porosity, and/or thickness) in a "MEASUREMENT VALUE(S) OUTPUT" step 370.

The various embodiments of the structures and methods of this invention that are described above are illustrative only of the principles of this invention and are not intended to limit the scope of the invention to the particular embodiments described. Thus, the invention is limited only by the following claims and their equivalents.

The invention claimed is:

1. A spectroscopic ellipsometry system comprising:
a near infra-red (NIR) beam generator for generating a NIR probe beam;
focusing optics for directing the NIR probe beam at a test sample;
a first array-based detector that measures a first range of NIR wavelengths;
a second array-based detector that measures a second range of NIR wavelengths;
output optics for directing an output beam reflected from the test sample in response to the NIR probe beam onto the first and second detectors; and
an analysis system for generating measurement results from data measured by the first and second detectors by modeling structures on the test sample as a layer of homogenous material, the analysis system including:
means for adjusting a thickness and an index of refraction for the layer of homogenous material until model results provided by the layer of homogenous material match the data measured; and
means for determining the measurement results for the test sample based on the thickness and the index of refraction for the layer of homogenous material.

2. The spectroscopic ellipsometry system of claim 1, wherein the first range comprises 0.7 to 0.9 µm,
wherein the first detector comprises a silicon photodiode array,
wherein the second range comprises 1.0 to 2.0 µm, and
wherein the second detector comprises a compound semiconductor photodiode array.

3. The spectroscopic ellipsometry system of claim 1, wherein the focusing optics comprises a polarizer, and wherein the output optics comprises an analyzer.

4. The spectroscopic ellipsometry system of claim 3, wherein the polarizer comprises a calcite polarizer, and wherein the analyzer comprises a calcite analyzer.

5. The spectroscopic ellipsometry system of claim 1, wherein the NIR beam generator comprises a visible light source.

6. A method for performing spectroscopic ellipsometry on a test sample, the method comprising:
directing a near infra-red (NIR) probe beam at the test sample to generate a reflected output beam;
measuring polarization data for the reflected output beam, wherein measuring polarization data includes:
measuring a first range of NIR wavelengths in the reflected output beam using a first array-based detector; and
measuring a second range of NIR wavelengths in the reflected output beam using a second array-based detector; and
generating measurement results for the test sample based on the polarization data by modeling structures in the test sample as a homogenous fictitious layer, wherein generating measurement results includes:
adjusting parameters for the homogenous fictitious layer until model results provided by the homogenous fictitious layer match the polarization data; and
determining the measurement results for the test sample based on the parameters for the homogenous fictitious layer.

7. The method of claim 6, wherein the parameters for the homogenous fictitious layer comprise layer thickness and layer index of refraction,
wherein the structures in the test sample comprise an array of trenches,
wherein determining the measurement results comprises providing the layer thickness as a depth for each of the array of trenches, and
wherein determining the measurement results further comprises determining a width for each of the array of trenches and a spacing between each of the array of trenches based on the layer index of refraction.

8. The method of claim 6, wherein directing the NIR probe beam at the test sample comprises generating the NIR probe beam using a visible light source.

9. The method of claim 6, wherein the first detector comprises a silicon diode array, and
wherein the second detector comprises a compound semiconductor diode array.

10. The method of claim 6, wherein directing the NIR probe beam at the test sample comprises passing the NIR probe beam through a polarizer, and
wherein measuring the polarization data for the reflected output beam comprises passing the reflected output beam through an analyzer.

11. A metrology system comprising:
means for directing a near infra-red (NIR) probe beam at a test sample to generate a reflected output beam;
means for measuring polarization data for the reflected output beam, the means for measuring polarization data including:
a first array-based detector that measures a first range of NIR wavelengths in the reflected output beam; and
a second array-based detector that measures a second range of NIR wavelengths in the reflected output beam; and
means for generating measurement results for the test sample based on the polarization data by modeling structures in the test sample as a homogenous fictitious layer, wherein the means for generating measurement results including:
means for adjusting parameters for the homogenous fictitious layer until model results provided by the homogenous fictitious layer match the polarization data; and
means for determining the measurement results for the test sample based on the parameters for the homogenous fictitious layer.

12. The metrology system of claim 11, wherein the means for directing the NIR probe beam comprises means for generating the NIR probe beam using a visible light source.

* * * * *